(12) United States Patent
Bracamonte-Sommer

(10) Patent No.: US 6,478,761 B2
(45) Date of Patent: Nov. 12, 2002

(54) ROLLABLE BODY PART PROTECTOR

(76) Inventor: Violeta Bracamonte-Sommer, 537 73rd St., Brooklyn, NY (US) 11209-2611

(*) Notice: Subject to any disclaimer, the term of this patent is extended or adjusted under 35 U.S.C. 154(b) by 0 days.

(21) Appl. No.: 09/377,601

(22) Filed: Aug. 19, 1999

(65) Prior Publication Data

US 2002/0007134 A1 Jan. 17, 2002

Related U.S. Application Data

(63) Continuation-in-part of application No. 09/127,725, filed on Aug. 3, 1998.

(51) Int. Cl.$^7$ ................................................. A61F 5/00
(52) U.S. Cl. ................................................. 602/22; 602/60
(58) Field of Search ........................... 602/6–8, 14, 19, 602/20–23, 26, 60–64, 75–77; 2/311, 312, 338, 220, 221, 236, 237, 170, 167, 163, 22, 21, 16, 166; 66/190, 202; 442/203–216; 428/98–100; 139/383 R, 386

(56) References Cited

U.S. PATENT DOCUMENTS

| | | | |
|---|---|---|---|
| 365,612 A | | 6/1887 | Lee |
| 2,310,082 A | * | 2/1943 | Holbrooke .................... 602/75 |
| 2,667,868 A | | 2/1954 | Smyth |
| 2,811,154 A | * | 10/1957 | Scholl .......................... 602/76 |
| 3,039,460 A | | 6/1962 | Chandler |
| 3,695,258 A | | 10/1972 | Castle |
| 4,207,885 A | * | 6/1980 | Hampton et al. ........... 128/156 |
| 4,215,684 A | | 8/1980 | Westip |
| 4,441,489 A | | 4/1984 | Evans et al. |
| 4,481,942 A | * | 11/1984 | Duncan ....................... 128/878 |
| 4,665,909 A | * | 5/1987 | Trainor ........................ 128/155 |
| 4,745,912 A | | 5/1988 | McMurray |
| 4,782,775 A | * | 11/1988 | Scher et al. ............ 112/470.33 |
| 4,899,737 A | | 2/1990 | Lazarian |
| 4,915,097 A | | 4/1990 | West |
| 4,941,460 A | | 7/1990 | Working |
| 4,991,234 A | * | 2/1991 | Greenberg ...................... 2/170 |
| 5,036,838 A | | 8/1991 | Sherman |
| 5,069,203 A | | 12/1991 | Anderson |
| 5,348,531 A | | 9/1994 | Brown et al. |
| RE34,753 E | | 10/1994 | Groiso |
| 5,353,812 A | * | 10/1994 | Chow .......................... 128/898 |
| 5,368,602 A | | 11/1994 | de la Torre |
| 5,480,709 A | * | 1/1996 | Sauvignet ............... 442/215 X |
| 5,692,236 A | * | 12/1997 | Prince ............................. 2/21 |
| 5,730,154 A | | 3/1998 | DeRidder |
| 5,746,707 A | | 5/1998 | Eck |
| 5,957,944 A | * | 9/1999 | Khuri et al. ................. 606/170 |
| 5,994,612 A | * | 11/1999 | Watkins ........................ 602/41 |

FOREIGN PATENT DOCUMENTS

| | | | | |
|---|---|---|---|---|
| GB | 113066 | * | 2/1918 | .................... 602/6 |
| GB | 1060729 | | 3/1967 | |

OTHER PUBLICATIONS

Medical Multimedia Group, Randale Sechrest, MD, Trigger Finger, http://www.sechrest.com/mmg/ctd/trigger.html (May 1996).

Thorpe, Results of surgery for trigger finger, J Hand Surg (May 1988): 199–201; Medline Abstract only, http://www.ncbi.nlm.nih.gov.

Bonnici & Spencer, A survey of "trigger finger" in adults, J Hand Surg [Br] 13(2): 202–203 (May 1988); Medline Abstract only, http://www.ncbi.nlm.nih.gov.

* cited by examiner

Primary Examiner—Denise Pothier
(74) Attorney, Agent, or Firm—Hall, Priddy Myers & Vande Sande

(57) ABSTRACT

A rollable protector, in particular a rollable splint, is disclosed that comprises fabric sheet(s). The fabric sheet is, in a first direction, stiff either inherently or as a consequence of rolling the sheet. In a second direction the fabric sheet is rollable. The stiffness of the sheet in the first direction allows to maintain a body part that is partially or fully encircled by the protector/splint to be kept in position. The splint is adjustable by fastener(s) to fit a body part of an individual user, is made of light material, is permeable to air, liquids or gels and can be washed.

39 Claims, 2 Drawing Sheets

ROLLABLE BODY PART PROTECTOR

CROSS-REFERENCE TO RELATED APPLICATION

This application hereby incorporates the disclosure of, is a continuation in part of, and claims under 35 U.S.C. §120 as its effective filing date, the filing date of the present inventor's prior copending U.S. patent application Ser. No. 09/127,725, filed on Aug. 3, 1998.

TECHNICAL FIELD

The present invention relates to protectors or supports such as splints, for the support or protection of an extremity or other body part. More particularly, the invention relates to a splint in the form of one or more sheets that is stiff in a first direction and rollable in a second direction.

BACKGROUND

Splints and other types of supports and protective means, per se, are well known in the medical art. Splints generally include a rigid member with some means of fastening the member to a body part. U.S. Pat. No. 3,695,258 to Castle discloses a disposable splint that is made of multiple sheets of material such as paper. The splint is stiff in a first direction and rollable in a direction perpendicular to said first direction. Other common means to support and protect body parts are elastic orthopedic bandages that are adjustable e.g. via a VELCRO™ fastener. U.S. Pat. No. 5,036,838 to Sherman discloses an orthopedic bandage that can include stays inserted between two layers of the fabric of the bandage to provide additional support for an extremity or other body part wrapped in said bandage.

The splint of the present invention was originally developed for the treatment of trigger finger. Trigger finger is a condition in which an afflicted finger spontaneously snaps into a flexed position when the finger is at rest. The afflicted finger then needs to be pulled into position. The snapping can cause sharp pain and swelling. A frequent cause of trigger finger is overuse of the afflicted finger.

The conventional treatment for trigger finger involves either injections whenever the problem occurs or surgery. The injections can be painful and the surgical treatment usually requires the patient to rest the operated finger for extended periods. The inventor of the present invention searched for alternative treatments for her trigger finger since she was not willing to either undergo further painful injections or to stop working for an extended period of time after a surgical intervention.

Since the snapping usually occurred at night she experimented with devices that she could wear at night to prevent her finger from snapping. Surprisingly, she found that wearing the inventive splint at night and taking it off during the day not only prevented the finger from snapping at night, but provided permanent relief. She no longer needs to wear the splint and is symptom free.

During further experimentation, she discovered that the inventive splint has wider application than the treatment of trigger finger. For example wearing the inventive splint on the toe next to her big toe relieved the pain of a bunion. U.S. Reissue Pat. No. 34,753 to Groiso mentions the use of rigid molded splints to treat trigger finger. However, Groiso failed to disclose treatment of trigger finger with splints similar to those of the present inventor. Thus, the present invention has, among other things, filled a need for splints that are easy to don and remove, and readily reuseable and useful in the treatment of trigger finger and for other purposes disclosed herein.

SUMMARY OF THE INVENTION

In a first aspect, the invention represents a splint for a body part which comprises at least one sheet of woven fabric. This sheet has, in a first direction, sufficient stiffness, when rolled and secured about the body part, to substantially resist bending of the body part. Moreover, the sheet is sufficiently compliant in a second direction, cross-wise relative to the first direction, to permit easy rolling of the sheet about the body part when the latter extends generally in said first direction. Finally, the splint comprises fastening means to secure the splint in rolled condition about the body part when the splint and sheet are rolled about a line extending in the first direction.

In another aspect, the invention is a splint for use on, and in caring for or treating, a body part of a living entity, said support comprising at least one thin sheet of fabric. In this aspect, the sheet has, extending in a first direction, a first set of fibers that are integrated with the weave of the sheet and that contribute to the sheet an amount of stiffness in the first direction which is sufficient, when the sheet is rolled and secured about the body part, to afford opposition against bending of the body part. Extending in a second direction in the sheet, said direction being cross-wise relative to the first direction, a second set of fibers is woven into the sheet, said second set of fibers and the sheet having sufficient flexibility to permit convenient manual rolling of the support about the body part when the latter is extended generally in the first direction. The sheet also has sufficient permeability to pass substances between the inner and outer surfaces of the rolled support. At least part of the sheet is a load-bearing portion of the support, non-hardenable under ordinary conditions of use, able to resist circumferential and/or bending loads. There is also at least one fastening device including hooks on a first portion of the splint and cooperating loops elsewhere on the splint to maintain the splint in rolled condition about the body part.

In still another aspect, the invention may or may not be a splint but in any event will constitute a support for use on, and in caring for or treating, a body part of any kind of living entity, whether of a human, an animal or a plant. The support comprises at least one sheet of woven fabric. The fabric has, extending in a first direction, a first set of members that are connected with the sheet and that contribute to the sheet an amount of stiffness in the first direction which is sufficient, when the sheet is rolled and secured about the body part, to afford support to the body part. Extending in a second direction in the sheet, said direction being cross-wise relative to the first direction, a second set of members is woven into the sheet. This second set of members and the sheet are sufficiently compliant to permit easy rolling of the sheet about the body part when the latter is extended generally in the first direction. At least part of the sheet, including at least part of the first set of members, is a load-bearing portion of the support. At least one fastener is secured to and positioned in or on the support to maintain the support in rolled condition about the body part.

In yet another aspect, the invention represents a method of treating trigger finger. The method comprises wearing, on at least one finger, a splint or support having the features of any of the foregoing aspects of the invention. In this method, the device is worn at any convenient time, and preferably during a period of sleep.

The invention also includes a variety of preferred embodiments in which the splints or other supports of any of the above-described aspects may have, be or include any one or any combination of the following features:

a span in the first direction which is at least a substantial portion of the length of, and is up to about the length of, a human digit;

a span in the first direction which is at least a substantial portion of the length of, and is up to about the length of, a human finger, and overlaps in its span at least two finger joints;

first and second edges separated from one another in the second direction and having sufficient expanse in the second direction to support the body part in the first direction when the support is rolled securely about said digit but having insufficient expanse in the second direction for the edges to overlap on another;

first and second edges separated from one another in the second direction and having sufficient expanse in the second direction for the edges to overlap one another when the support is rolled securely about said digit;

an overlap which is at least 20% of the diameter of the rolled support, or which extends about less than the entire periphery of the support, or which is up to 50% of the diameter of the rolled support;

not hardenable;

sufficient permeability to pass substances between the inner and outer surfaces of the rolled support;

a fastening device that comprises hook means on a first portion of the support and cooperating loop means elsewhere on the support to maintain the support in rolled condition about said body part;

hook means and loop means that respectively comprise hook fabric and loop fabric;

hook fabric and loop fabric that are each within the outline of the sheet;

hook fabric which extends outside the outline of the sheet;

first and second edges separated from one another in the second direction and have sufficient expanse in the second direction for the edges to overlap one another when the support is rolled securely about said digit and wherein the hook fabric is at one of the edges and the loop fabric is at the other of the edges;

hook fabric and loop fabric which are in the form of elongated strips located at said edges and running along said edges substantially in the first direction; at least one or both of said strips extending substantially throughout the span of the support in the first direction;

as a fastening device, an adhesive bond between overlapping portions of the support;

fabric with a weave including warp and weft formed of materials of differing stiffness, one of which is semi-rigid and the other of which is soft and pliable;

fabric with a weave including warp with a stiffness similar to that of the bristles of a hairbrush and weft in the form of compliant thread;

fabric that includes thermoplastic fibers;

fabric that is partly or fully resin-coated;

at least one sheet, including a sheet or a combination of sheets, which represents a major load-bearing member, or the sole load-bearing member, of the support;

a single sheet of the fabric which may represent a major load-bearing member, or the sole load-bearing member, of the support;

configured in such a way that the cross-wise second direction is perpendicular to the first direction;

configured in such a way that the cross-wise second direction is not perpendicular to the first direction;

resistant to degradation upon washing.

ADVANTAGES OF THE INVENTION

The present invention provides a new and improved support, which may be a splint, in form of one or more sheets of fabric that provides support in a first direction and is rollable in a second direction.

Various embodiments of the invention will provide one, more and in some cases all of the following advantages:

The support of the present invention is easy to put on, to remove, to replace and is adjustable in size. In a preferred embodiment the splint is permeable to air. Permeability to air reduces the risk of swelling of an supported body part and allows for combination treatments that might be impossible or at least difficult to administer with splints that do not have the same degree of permeability. Permeability to air also contributes to wearing comfort, which may speed up the healing process of a body part since the user may be willing to wear the splint over longer periods than e.g. a conventional bandage. Such a splint can be readily fabricated of materials that can withstand sterilization. The light weight, thinness and washability of the splint constitute further advantages that can be expected to contribute significantly to user-acceptance.

Other advantages will be apparent from the disclosure which follows and from use of the invention.

BRIEF DESCRIPTION OF THE DRAWINGS

A non-limiting embodiment of the invention, described in text which follows, is shown in accompanying illustrations, of which.

DESCRIPTION OF VARIOUS EMBODIMENTS OF THE INVENTION

Figure 1:
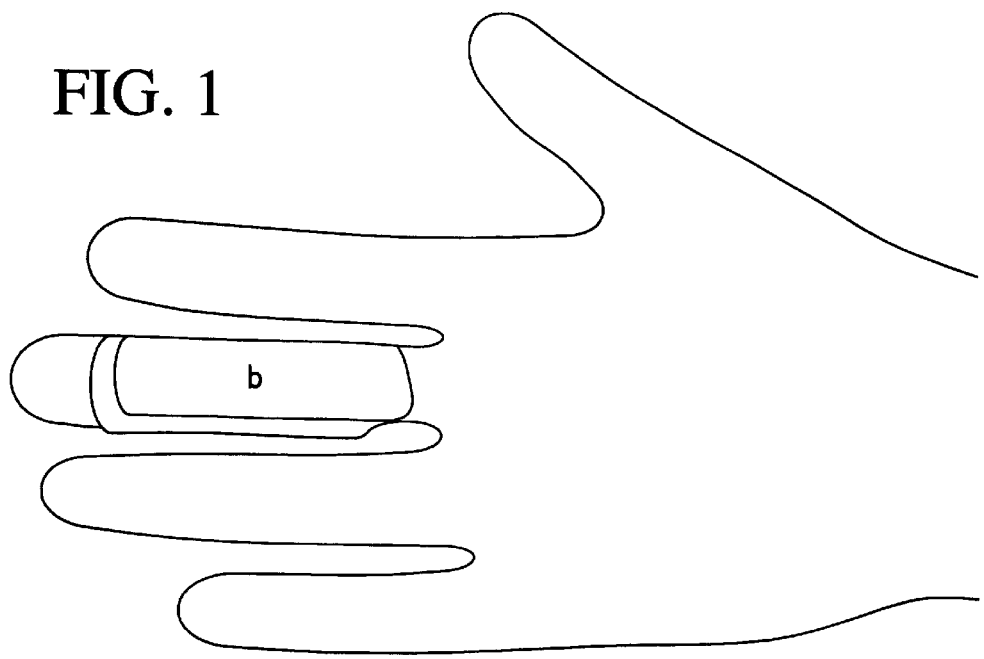
FIG. 1 shows an embodiment of inventive splint attached to finger.

The splint which is the preferred of the current invention is made from one or more sheets of fabric with one or more fastening means attached thereto. The sheet(s) of fabric have a first set of fibers connected to or woven into said sheet which contribute to the stiffness in a first direction. The fabric might either be inherently stiff in that direction or might become stiff as a consequence of being rolled. A second set of fibers are woven into said sheet and have sufficient flexibility to render the sheet rollable in a second direction. In a preferred embodiment the second set of fibers are substantially perpendicular to said first set of fibers.

"Stiff" and "stiffness" in the context of the present invention generally means at least rigid enough to substantially oppose or prevent bending of the body part to which the splint is secured or which the splint encloses in a substantially extended position. Stiffness might be inherent or might be a consequence of rolling the sheet into a second direction. However, certain applications might benefit from having complete rigidity in the first direction while others might benefit from some degree of flexibility in the set of fibers extending in the first direction. Thus, the terms "stiff" and "stiffness" include splints of the stiffness that allow for complete rigidity or limited flexibility suitable for the intended end use of the device.

In a preferred embodiment, the sheet of fabric is a woven fabric with a warp and a weft of different material. Either the warp or weft may be made of stiff bristle-like material while the other (warp or weft) is made of compliant thread. Different thermoplastic materials might impart sufficient stiffness to form the bristle-like material of the warp or weft. However, the present invention is also directed to splints made of fabric sheets in which warp or weft are made of the same material. Stiffness in one direction relative to the other can be accomplished by either simple rolling of the sheet in a second direction, pretreating the warp or weft set of fibers with stiffener or softener or by incorporating a higher amount of fibers either into the warp or the weft.

A material that has proven particularly useful in the current invention is BAN ROL (58% nylon, 14% rayon, 15% polyester, 10% thermoplastic resin), which is sold as a waist band stiffener. BAN ROL has a number of advantages including being stiff in one direction and easily rollable into a second direction which is substantially perpendicular to said first direction. In addition, BAN ROL is substantially uniform throughout and thus facilitates the manufacture of splints and provides a high level of comfort for the user. BAN ROL is also permeable to air and washable.

However, any other fabric sheet that is stiff in one direction or becomes stiff in one direction due to rolling into a second direction and which is rollable into a second direction can be used for splints of the current invention. Many materials used as waistbands fulfill these requirements. However, any other type of fabric might be used, for example materials that contain one or more types of polymeric material, to attain the desired properties of the fabric sheet. The materials used for the splint can also be partially or fully coated with materials such as resin, plastic or wax. The splint may also have ribs and other structures attached to or integrated therein. Such ribs and other structures may contribute to the splint's stiffness. Fasteners such as the ones discussed below could in some instances also contribute to the stiffness of the splint. The splint might also be fitted with cushioning material. For example, a splint designed for use at a wrist or arm might be provided with stripes of cushioning material. In a preferred embodiment the splint material is penetrable by air and easy to wash.

The splint can be manufactured in different sizes and for different body parts. For example toe splints could be manufactured that are shorter than finger splints. However, in a preferred embodiment, adjustability is built into the splint construction by adjustable fastening mean(s).

Advantageously, sides and edges of the inventive splint are treated to prevent unraveling of the fabric sheet. Depending on the material used, unraveling can be prevented e.g. by sewing an edge around the entire or parts of the splint that are prone to unravelling. Alternatively, a heat seal may be formed by melting a thermoplastic portion of the sheet material at the sides and edges of the splint to prevent unravelling.

When multiple sheets of fabric are used the sheets can be attached to each other in any convenient way such as gluing, sewing or thermobonding. If a glue is used such a glue is preferably resistant to washing.

The splint may be fastened to body parts by different types of fasteners. In its simplest form the splint might be bound on the body part with adhesive tape or provided at one edge with a glue strip that, after wrapping the splint around the body part, would stick to the opposite edge of the splint. Most glues in use today only allow for one time gluing or a limited number of detachments and reattachments. A one time gluing or "permanent" fastener might for example be advantageously used for applications where accidental or intended manipulation of the splint should be avoided, such as when the splint is used on a body part of a small child.

The splint is put on a body part such as a digit by wrapping the splint around the finger or toe and fastening it to the finger. The splint thus forms a cylinder which can, in a preferred embodiment, be slipped on and off in the same manner as taking a ring off and on a finger. In another preferred embodiment the vertical edges of the splint overlap to strengthen the splint. The overlap is preferably 20% to 50% of the diameter or preferably 20% to 50% of the circumference of the cylinder formed by the splint. An overlap can provide substantial additional stiffness without significantly increasing the weight or bulk of the splint. While some overlap is preferred, overlap is not essential.

The current invention also contemplates embodiments in which only parts of a body part such as a finger are covered by the splint. The minimum amount of splint material used is determined by the minimum amount of splint material necessary to carry out a desired function.

Figure 2:
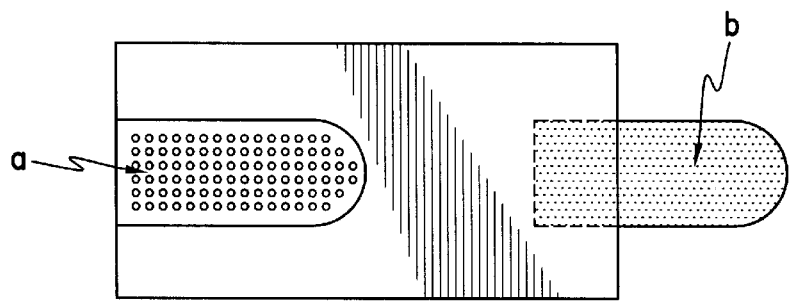
FIGS. 2, 3, 4 and 5 show embodiments of the splint with various configurations of fastening means (a, b) attached thereto.
Figure 3:
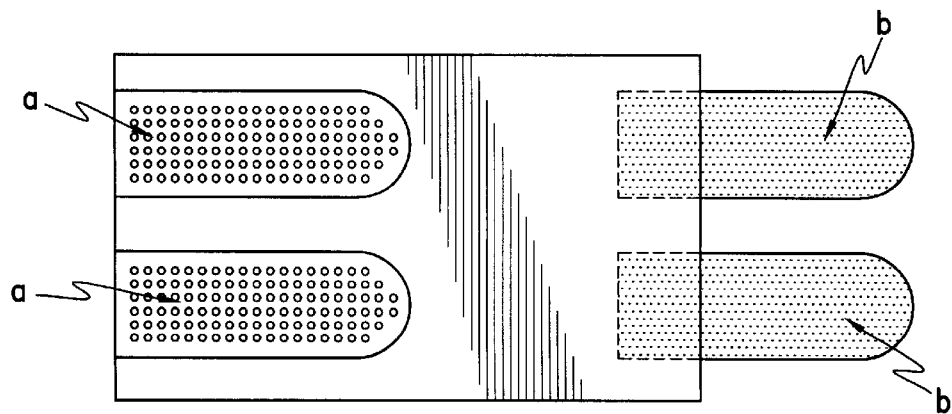
Figure 4:
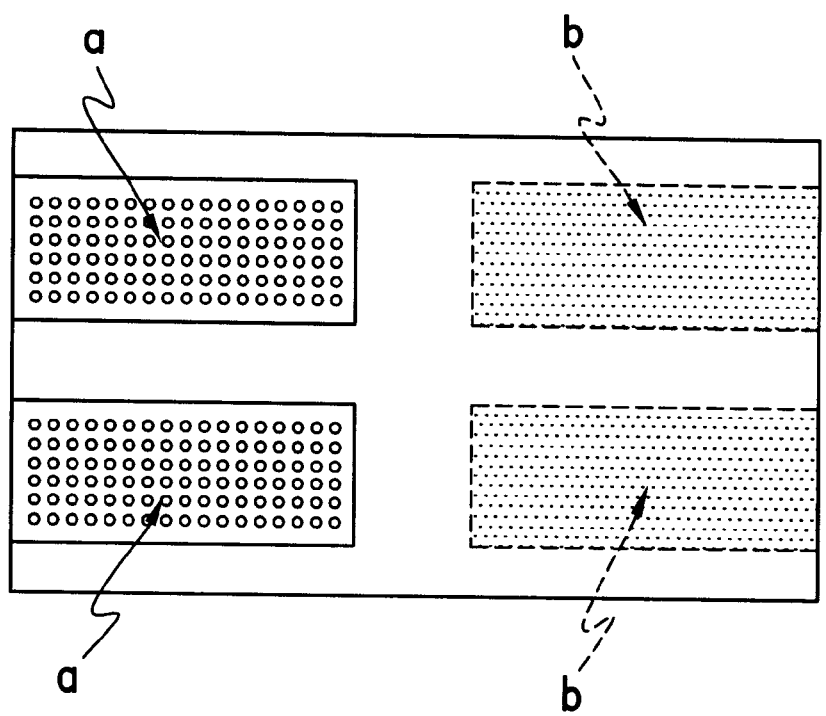
Figure 5:
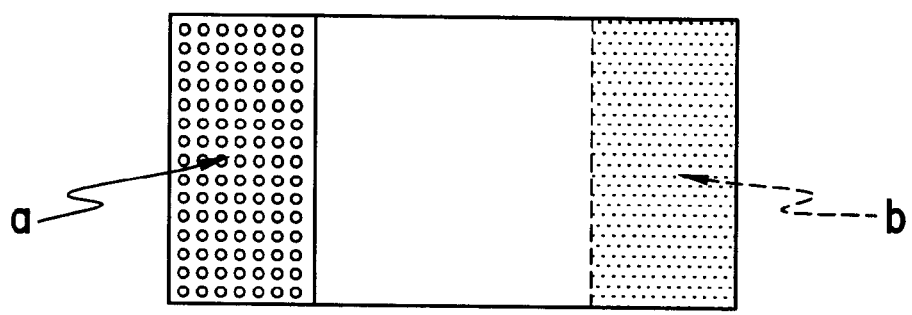

In certain preferred embodiments the fastening device is a VELCRO™ type hook and loop fastener, which can be attached to the fabric sheet in different configurations and in single or multiple sets. Some preferred configurations are shown in FIGS. 2 to 5. FIG. 1 shows the splint of FIG. 2 in place. FIGS. 2 to 5 show fasteners that are composed of hook and loop parts a and b. For example, a in each of the drawings represents a hook portion of the fastener which is attached to one face of the splint and b in each of the drawings represents the loop portion of the fastener which is attached to the other part of the splint. In a preferred embodiment of the VELCRO™ type fastener, the splint is wrapped so that the rougher part faces outward and the softer part, if any, touches the body of the user. FIG. 2 shows an embodiment in which the hook and loop parts of the fastener are placed medially on opposite ends of the splint and part b extends beyond the edge of the splint. FIG. 3 shows the splint with a pair of fasteners with parts b of the fasteners extending beyond the edge of the splint. The embodiments of FIGS. 2 and 3 allow adjustability for a wide variety of circumferences of a body part. FIG. 4 shows a splint with two pairs of fasteners wherein all parts of the fasteners are located within the area of the splint. FIG. 5 shows a splint with a fastener comprising a single pair of hook and loop parts which are placed vertically at the ends of the splint. The splint of FIG. 5 has a high degree of rigidity and is particularly easy to apply to a toe.

Any other type of fastener that can hold the splint to a body part might be used for the current invention. Non-limiting examples are plastic and metal snaps, different type of buckles, metal or plastic hook and eye fasteners or old fashioned ACE bandage type fasteners. Adjustable hook and eye closures with multiple eyes in a row as sold by Prym-Dritz Corp. could be particularly useful for splints used for large body parts such as arms and legs.

USES OF THE INVENTION

The present invention can be used for any condition of a body part that might benefit from wearing a splint or other protection. Some of the uses of these are illustrated below.

The protector might be used to protect body parts from external influences such a rubbing or touching. For example, the invention has been applied to a toe to provide lasting relief the pain of bunions at an adjacent toe.

The splint might also be used to maintain a body part in a particular position, such as an extended position. As discussed above, the invention can serve as a splint in treating trigger finger. In this application the user might choose to wear the splint all the time or wear it only at night time for e.g. a number of weeks. The ability of the invention to act as a support to maintain a body part in an extended position can also be used to promote the healing process of broken bones, sprains or strains.

Since the device can be designed to be permeable to air and for liquids and for gels, it can be used for the treatment of conditions in which a body part that needs protection and/or support also benefits from aeration or application of gases, liquids, gels or the like. An example could be a case where a supported body part also is subject to a topical treatment that works better when the treated body part is exposed to air.

The foregoing disclosures of embodiments of the invention and uses therefor have been given merely for purposes of illustration and not to limit the invention. Thus, the invention should be considered to include all embodiments falling within the scope of the following claims and equivalents thereof.

What is claimed is:

1. A method of treating trigger finger comprising wearing, on at least one finger, a splint, said splint comprising:
    A. at least one thin sheet of fabric which has,
        1. extending in a first direction, a first set of fibers that are integrated with the weave of the sheet and that contribute stiffness to the sheet in said first direction, wherein said first direction is defined by a longitudinal axis, wherein said longitudinal axis is the axis created by rolling the sheet in a second direction, and
        2. extending in said second direction in the sheet, a second set of fibers woven into the sheet cross-wise relative to the first direction, the second set of fibers and the sheet having sufficiently flexibility to permit convenient manual rolling of the support,
        3. wherein said sheet allows for substances to pass between the inner and outer surfaces of the rolled support,
    at least part of the sheet being a non-hardenable load-bearing portion of the support that is able to resist circumferential and/or bending loads, and
    B. at least one fastening device including hooks on a first portion of the splint and cooperating loops elsewhere on the splint to maintain the splint in rolled condition about the body part.

2. A method according to claim 2 wherein the hooks and loops respectively comprise hook fabric and loop fabric.

3. A method according to claim 2 wherein the hook fabric and loop fabric are each within the outline of the sheet.

4. A method according to claim 2 wherein the hook fabric extends outside the outline of the sheet.

5. A method according to claim 1 wherein the hook fabric and loop fabric are in the form of elongated strips located at edges of the at least one sheet and extending substantially in said longitudinal direction.

6. A method according to claim 5 wherein at least one of said strips extends substantially throughout the span of the splint in said longitudinal direction.

7. A method according to claim 5 wherein both of said strips extend substantially throughout the span of the splint in said longitudinal direction.

8. A method according to claim 1 wherein the fabric of said sheet includes thermoplastic fibers.

9. A method according to claim 1 wherein the fabric of said sheet is partly or fully resin-coated.

10. A method according to claim 1 wherein the splint has a single sheet of the fabric.

11. A method according to claim 1 wherein the splint is resistent to degradation upon washing.

12. A method according to claim 1 wherein said splint is worn during a period of sleep.

13. A method of treating trigger finger comprising wearing, on at least one finger, a splint in the form of a rollable protector, comprising:
    at least one sheet of rollable woven fabric,
    at least one fastening device to secure the woven fabric in a rolled position,
    wherein, when rolled, the fabric defines a longitudinal axis, said fabric having stiffness in the direction of said axis and being compliant in a direction cross-wise of said axis to allow rolling of the fabric about said axis.

14. A method according to claim 13 wherein the protector is non-hardenable under ordinary conditions of use.

15. A method according to claim 13 wherein the protector has sufficient permeability to allow a substance to pass between the interior of the rolled protector and the outer surface thereof.

16. A method according to claim 15, wherein the substance is moisture that passes from the interior of the rolled splint to the outer surface thereof.

17. A method according to claim 13 wherein the fastening device of the protector comprises hook means on a first portion of the protector and cooperating loop means elsewhere on the protector to maintain the protector in rolled condition about a body part.

18. A method according to claim 17 wherein the hook means and loop means respectively comprise hook fabric and loop fabric.

19. A method according to claim 18 wherein the hook fabric and loop fabric are each within the outline of the sheet.

20. A method according to claim 18 wherein the hook fabric extends outside the outline of the sheet.

21. A method according to claim 18 wherein the hook fabric and loop fabric are in the form of elongated strips located at edges of the at least one sheet and extending substantially in said longitudinal direction.

22. A method according to claim 21 wherein at least one of said strips extends substantially throughout the span of the protector in said longitudinal direction.

23. A method according to claim 21 wherein both of said strips extend substantially throughout the span of the protector in said longitudinal direction.

24. A method according to claim 13 wherein the fastening device of the protector is adhesive material for forming a bond between edge portions of the protector.

25. A method according to claim 13 wherein the fabric of the protector has a weave including warp and weft formed of materials of differing stiffness, one of which is semi-rigid and the other of which is soft and pliable.

26. A method according to claim 13 wherein the fabric of the protector includes thermoplastic fibers.

27. A method according to claim 13 wherein the fabric of the protector is partly or fully resin-coated.

28. A method according to claim 13 wherein said at least one sheet of the protector, including a sheet or a combination of sheets, represents a major load-bearing member of the protector.

29. A method according to claim 13 wherein said at least one sheet of the protector, including a sheet or a combination of sheets, represents the sole load-bearing member of the protector.

30. A method according to claim 13 wherein the protector has a single sheet of the fabric.

31. A method according to claim 30 wherein said at least one sheet represents a major load-bearing member of the protector.

32. A method according to claim 30 wherein said at least one sheet represents the sole load-bearing member of the protector.

33. A method according to claim 13 wherein said crosswise direction of said longitudinal axis defined by the fabric of the protector is perpendicular to said longitudinal axis.

34. A method according to claim 13 wherein said crosswise direction of said longitudinal axis defined by the fabric of the protector is not perpendicular to said longitudinal axis.

35. A method according to claim 13 wherein the protector is resistant to degradation upon washing.

36. A method according to claim 13, wherein said at least one sheet of woven fabric of the protector has, extending in the direction of said axis, a first set of members that are connected with the sheet and that contribute to the sheet stiffness in the direction of said axis.

37. A method according to claim 13 wherein said protector is worn during a period of sleep.

38. A rollable protector according to claim 13 wherein the method fabric resists stretching in said direction cross-wise of said axis.

39. A method according to claim 13, wherein said at least one sheet of woven fabric of the protector has, extending in the direction of said axis, a first set of members that are connected with the sheet and that contribute to the sheet stiffness in the direction of said axis.

* * * * *